US007829573B2

United States Patent
Curwen et al.

(10) Patent No.: US 7,829,573 B2
(45) Date of Patent: Nov. 9, 2010

(54) THERAPEUTIC COMBINATIONS OF ANTIHYPERTENSIVE AND ANTIANGIOGENICS AGENTS

(75) Inventors: Jon Owen Curwen, Macclesfield (GB); Donald James Ogilvie, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/240,413

(22) PCT Filed: Apr. 2, 2001

(86) PCT No.: PCT/GB01/01522

§ 371 (c)(1),
(2), (4) Date: Oct. 1, 2002

(87) PCT Pub. No.: WO01/74360

PCT Pub. Date: Oct. 11, 2001

(65) Prior Publication Data

US 2003/0144298 A1 Jul. 31, 2003

(30) Foreign Application Priority Data

Apr. 5, 2000 (GB) ................................ 0008269.3

(51) Int. Cl.
*A61K 31/401* (2006.01)
*A61K 31/505* (2006.01)
(52) U.S. Cl. ................ 514/266.2; 514/266.22
(58) Field of Classification Search ............ 514/266.1, 514/266.3, 423, 428
See application file for complete search history.

(56) References Cited

U.S. PATENT DOCUMENTS

| 5,350,751 A | 9/1994 | Wagner et al. |
| 5,440,046 A | 8/1995 | Wagner et al. |
| 5,646,136 A | 7/1997 | Petrow et al. ............... 514/167 |
| 6,191,144 B1 | 2/2001 | Isner ......................... 514/315 |

(Continued)

FOREIGN PATENT DOCUMENTS

WO       WO 97/30035 A1 *  8/1997

(Continued)

OTHER PUBLICATIONS

Hardman, J. G., Editor-in-Chief, Goodman & Gilman's The Pharmacological Basis of Therapeutics, 9th Edition, Chapter 33, Antihypertnesive Agents and the Drug Therapy of Hypertension, pp. 780-805, 1996.*

(Continued)

*Primary Examiner*—Sharmila Gollamudi Landau
*Assistant Examiner*—Kortney L Klinkel
(74) *Attorney, Agent, or Firm*—Morgan, Lewis & Bockius LLP

(57) ABSTRACT

The invention concerns the use of a combination of an anti-angiogenic agent and an anti-hypertensive agent for use in the manufacture of a medicament for the treatment of a disease state associated with angiogenesis in a warm-blooded mammal, such as a human being. The invention also relates to pharmaceutical compositions comprising an anti-angiogenic agent and an anti-hypertensive agent, to kits thereof and to a method of treatment of a disease state associated with angiogenesis which comprises the administration of an effective amount of a combination of an anti-angiogenic agent and an anti-hypertensive agent to a warm-blooded animal, such as a human being.

6 Claims, 1 Drawing Sheet

U.S. PATENT DOCUMENTS

| | | | |
|---|---|---|---|
| 6,455,283 B1 * | 9/2002 | Ferrara et al. | 435/69.4 |
| 7,074,800 B1 * | 7/2006 | Stokes et al. | 514/266.2 |
| 7,166,625 B2 * | 1/2007 | Egan et al. | 514/374 |
| 2003/0191055 A1 * | 10/2003 | Epstein et al. | 514/12 |
| 2005/0043395 A1 | 2/2005 | Wedge | |
| 2005/0222183 A1 | 10/2005 | Wedge | |
| 2005/0245549 A1 | 11/2005 | Wedge | |
| 2006/0009418 A1 | 1/2006 | Barge | |
| 2006/0142316 A1 | 6/2006 | Wedge et al. | |
| 2006/0160775 A1 | 7/2006 | Wedge | |
| 2006/0167024 A1 | 7/2006 | Wedge | |
| 2006/0167027 A1 | 7/2006 | Wedge et al. | |
| 2006/0223815 A1 | 10/2006 | Curwen et al. | |
| 2007/0135462 A1 | 6/2007 | Wedge | |
| 2008/0015205 A1 | 1/2008 | Wedge | |
| 2008/0113039 A1 | 5/2008 | Wedge | |
| 2008/0119479 A1 | 5/2008 | Wedge | |
| 2008/0125447 A1 | 5/2008 | Wedge | |
| 2008/0200436 A1 | 8/2008 | Wedge | |
| 2008/0269261 A1 | 10/2008 | Wedge et al. | |
| 2008/0306094 A1 | 12/2008 | Wedge | |
| 2009/0123474 A1 | 5/2009 | Blakey et al. | |
| 2009/0176731 A1 | 7/2009 | Wedge | |

FOREIGN PATENT DOCUMENTS

| | | |
|---|---|---|
| WO | WO 98/28006 | 7/1998 |
| WO | WO 00/13703 | 3/2000 |
| WO | 00/47212 A | 8/2000 |
| WO | WO 01/32651 A1 * | 10/2001 |
| WO | WO 03/039551 | 5/2003 |
| WO | WO 2004/014383 | 2/2004 |
| WO | WO 2004/014426 | 2/2004 |
| WO | WO 2004/032937 | 4/2004 |
| WO | WO 2004/071397 | 8/2004 |
| WO | WO 2004/098604 | 11/2004 |
| WO | WO 2005/004870 | 1/2005 |
| WO | WO 2005/004871 | 1/2005 |
| WO | WO 2005/004872 | 1/2005 |
| WO | WO 2005/092303 | 10/2005 |
| WO | WO 2005/092384 | 10/2005 |
| WO | WO 2005/092385 | 10/2005 |
| WO | WO 2006/035203 | 4/2006 |
| WO | WO 2006/035204 | 4/2006 |
| WO | WO 2006/048633 | 5/2006 |
| WO | WO 2007/003933 | 1/2007 |
| WO | WO 2007/068895 | 6/2007 |
| WO | WO 2007/071958 | 6/2007 |
| WO | WO 2007/071970 | 6/2007 |
| WO | WO 2008/037996 | 4/2008 |
| WO | WO 2008/125820 | 10/2008 |

OTHER PUBLICATIONS

Ku., D. D. et al., American Physiological Society, H586-H591, 1993.*

Horowitz et al. Vascular endothelial growth factor/vascular permeability factor produces nitric oxide-dependent hypotension. Arteriosclerosis, thrombosis, and Vascular Biology. 1997;17:2793-2800, electronic copy, pp. 1-16.*

Edwards et al. Transport of [3H]Losartan across isolated perfused rabbit proximal tubule. The Journal of Pharmacology and Experimental Therapeutics. 1999; 290 (No. 1): 38-42.*

Landzberg et al. (Landzberg et al. Pathophysiology and pharmacological approaches for prevention of coronary artery restenosis following coronary artery balloon angioplasty and related procedures. Progress in Cardiovascular Diseases. 1997; vol. XXXIX, No. 4: 361-398.*

Kaplan. Angiotensin II receptor antagonists in the treatment of hypertension. American Family Physician. 1999;60:1185-1190, electronic pp. 1-7.*

Hennequin et al. (J. Med. Chem. 1999, 42(26), 5369-5389).*

"Acidic and Basic FGFs Dilate Arterioles of Skeletal Muscle Through a NO-Dependent Mechanism" by H. Mac Wu et al., Amer. Physiological Soc., 1996.

"Nitric Oxide Mediates Mitogenic Effect of VEGF on Coronary Venular Endothelium" by Morbidelli et al., Amer. Physiological Society, 1996.

"Cardiovascular Effects of Basic Fibroblast Growth Factor in Rats" by Boussairi et al., Journal of Cardiovascular Pharmacology, 1994.

"Effects of Vascular Endothelial Growth Factor on Hemodynamics and Cardiac Performance" by Yang et al., Journal of Cardiovascular Pharmacology, 1996.

"Role of Vascular Endothelial Cell Growth Factor in Ovarian Hyperstimulation Syndrome" by Levin et al., Journal of Clinical Investigation, vol. 102, No. 11, Dec. 19998.

"Phase I Safety and Pharmacokinetic Study of Recombinant Human Anti-Vascular Endothelial Growth Factor in Patients with Advanced Cancer", by Gordon et al., Journal of Clinical Oncology, vol. 19, No. 3, Feb. 1, 2001.

"Vascular Endothelial Growth Factor Induces EDRF-dependent Relaxation in Coronary Arteries" by David D. Ku et al., American Physiological Society, 1993.

Karamsetty et al, 2001, *Jnl. Pharmacol. and Experimental Therapeutics*, vol. 297, No. 3, pp. 968-974.

Levitzki, A. and Gazit, A. "Tyrosine Kinase Inhibition: An Approach to Drug Development", *Science* 267 (5205): 1782-1788, 1995.

Li, J.S., Knaf O. L., Turgeon A. et. al. "Effect of Endothelin Antagonism on Blood Pressure and Vascular Structure in Renovascular hypertensive rats" *Am. Jnl. Physiol. Heart Circ. Physiol.* 271: H88-H93, 1996.

Lopez, J.J., Laham, R.J., Carrozza, J.P et. al. (1997) Haemodynamic Effects of Intracoronary VEGF Delivery: Evidence of Tachyphylaxis and NO Dependence of Response, *Am. J. Physiol.* 273, H1317-H1323.

Nestel et al, 1999, *Jnl. Clin. Endocrinology & Metabolism*, vol. 84, No. 5, pp. 895-898.

Rivas et al, 2002, *Jnl. of Nutrition*, 132, pp. 1900-1902.

* cited by examiner

US 7,829,573 B2

THERAPEUTIC COMBINATIONS OF ANTIHYPERTENSIVE AND ANTIANGIOGENICS AGENTS

CROSS-REFERENCE TO RELATED APPLICATIONS

This application is a national stage filing under 35 U.S.C. 371 of International Application No. PCT/GB01/01522, filed Apr. 2, 2001, which claims priority from GB Application No. GB 0008269.3, filed Apr. 5, 2000, the specification of each of which are incorporated by reference herein. International Application No. PCT/GB01/01522 was published under PCT Article 21(2) in English.

STATEMENT REGARDING FEDERALLY SPONSORED RESEARCH OR DEVELOPMENT

None.

INCORPORATION-BY-REFERENCE OF MATERIAL SUBMITTED ON A COMPACT DISC

None.

BACKGROUND OF THE INVENTION

The present invention relates to a method for the treatment of a disease state associated with angiogenesis by the administration of an anti-angiogenic agent and an anti-hypertensive agent, to a pharmaceutical composition comprising an anti-angiogenic agent and an anti-hypertensive agent, to a kit comprising an anti-angiogenic agent and an anti-hypertensive agent, and to the use of an anti-angiogenic agent and an anti-hypertensive agent in the manufacture of a medicament for use in the production of an anti-angiogenic effect in warm-blooded animals, such as humans.

Angiogenesis, the process of forming new blood vessels, plays an important role in a variety of normal processes including embryonic development, wound healing and several components of female reproductive function. However, undesirable or pathological angiogenesis has been associated with a number of disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31).

Angiogenesis is stimulated via the promotion of the growth of endothelial cells. Several polypeptides with in vitro endothelial cell growth promoting activity have been identified including, acidic and basic fibroblast growth factors (aFGF & bFGF) and vascular endothelial growth factor (VEGF). The growth factor activity of VEGF, in contrast to that of the FGFs, is relatively specific towards endothelial cells, by virtue of the restricted expression of its receptors. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Alteration of vascular permeability is also thought to play a role in both normal and pathological physiological processes (Cullinan-Bove et al, 1993, Endocrinology 133: 829-837; Senger et al, 1993, Cancer and Metastasis Reviews, 12: 303-324).

Thus antagonism of the activity of VEGF is expected to be beneficial in a number of disease states, associated with angiogenesis and/or increased vascular permeability, such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. For example, antagonism of VEGF action by sequestration of VEGF with anti-body can result in inhibition of tumour growth (Kim et al, 1993, Nature 362: 841-844).

VEGF binds to a receptor with intrinsic tyrosine kinase activity, a so-called receptor tyrosine kinase (RTK). RTKs are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De-Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

Compounds which are inhibitors of VEGF receptor tyrosine kinase are described, for example in, International Patent Applications Publication Nos. WO 97/22596, WO 97/30035, WO 97/32856, WO 97/34876, WO 97/42187, WO 98/13354, WO 98/13350, WO 99/10349, WO 00/21955 and WO 00/47212.

In the normal mammal blood pressure is strictly controlled. This is facilitated by a complex interaction of a number of mediators, whose effects are maintained at an equilibrium. The system is such that if the level of one mediator changes this is compensated for by the other mediators such that normal blood pressure is maintained. (for a review of the systems which maintain blood pressure the reader is referred to: Guyton et al 1972 Annual Review of Physiology 34, 13-46; and Quan et al 1997 Pacing and Clinical Electrophysiology 20, 764-774). It is important that blood pressure is tightly controlled because hypertension, high blood pressure, underlies a variety of cardiovascular diseases, such as stroke, acute myocardial infarction, and renal failure.

A number of substances exhibit effects on blood vessels in vitro which in isolation would suggest effects on blood pressure in vivo. However, because of the nature of the control of blood pressure often any effects in vivo are compensated for and thus normal blood pressure is maintained.

It has been reported that VEGF and FGF have acute effects on vascular tone. VEGF has been shown to dilate coronary arteries in the dog in vitro (Ku et. al., 1993, Am J Physiol 265:H585-H592) and to induce hypotension in the conscious rat (Yang et. al., 1996, J Cardiovasc Pharmacol 27:838-844). However, in vivo these effects are only transitory. Even with a very large dose of VEGF (250 μg/kg) in conscious rats Yang et al observed a return to normal blood pressure within 20 minutes, at lower doses blood pressure returned to normal significantly faster. Boussairi et. al. have observed a similar effect upon administration of bFGF to anaesthetised rats, with the blood pressure returning to normal within 30 minutes after addition of 15 µg/kg bFGF (J Cardiovasc Pharmacol 1994 23:99-102). These studies also show that tachyphylaxis (or desensitisation) quickly develops following growth factor administration. Thus further administration of growth factor has no effect on blood pressure.

It has been reported that the vasodilation induced by both FGF and VEGF depends, at least in part, on the release of nitric oxide (NO), also referred to as endothelially derived relaxant factor (EDRF), (Morbidelli et. al., 1996, Am J Physiol 270:H411-H415 and Wu et. al., 1996, Am J Physiol 271:H1087-H1093).

In International Patent Application Publication No. WO 98/28006 a method for treating a hypertensive disorder in a pregnant woman is described, the method comprising administering to the pregnant woman an amount of a therapeutic substance which regulates the amount, and/or activity of, VEGF. In International Patent Application Publication No. WO 00/13703 is described a method for treating hypertension comprising administering to a patient an effective amount of an angiogenic factor such as VEGF, or an agonist thereof.

BRIEF SUMMARY OF THE INVENTION

Whilst administration of high levels of VEGF to conscious rats only produces a transient decrease in blood pressure, which cannot be maintained due to tachyphylaxis, we have found surprisingly that a VEGF receptor tyrosine kinase inhibitor leads to a sustained increase in blood pressure in rats when administered more than once, particularly when administered chronically. Thus the present invention relates to ways in which an antiangiogenic effect may be produced in a warm-blooded animal, such as a human being, without causing hypertension.

DETAILED DESCRIPTION OF THE INVENTION

Figure 1:
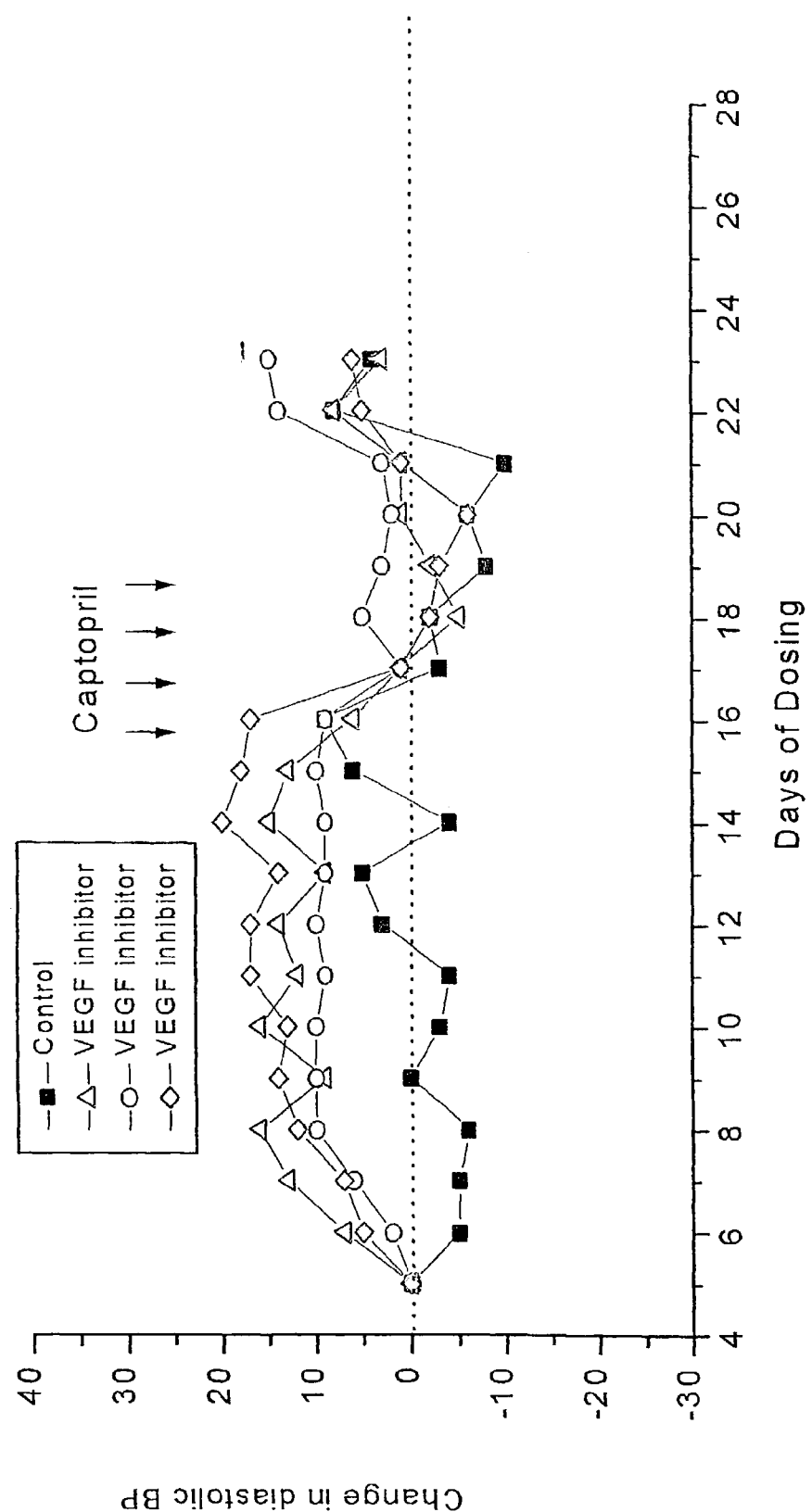
FIG. 1 shows the effect of the VEGF receptor-tyrosine kinase inhibitor [4-(bromo-2-fluoroanilino)-6-methoxy-7-(1-methylpiperidin-4-ylmethoxy)quinazoline] on the distolic blood pressure in rats as discussed in Example 1.

Thus according to the present invention there is provided a method of treatment of a disease state associated with angiogenesis which comprises the administration of an effective amount of a combination of an anti-angiogenic agent and an anti-hypertensive agent to a warm-blooded animal, such as a human being.

According to a further feature of the present invention there is provided the use of a combination of an anti-angiogenic agent and an anti-hypertensive agent for use in the manufacture of a medicament for the treatment of a disease state associated with angiogenesis in a warm-blooded mammal, such as a human being.

According to a further feature of the present invention there is provided a pharmaceutical composition comprising an anti-angiogenic agent and an anti-hypertensive agent for the treatment of a disease state associated with angiogenesis in a warm-blooded mammal, such as a human being.

According to a further aspect of the present invention there is provided a method for producing an anti-angiogenic and/or vascular permeability reducing effect in a warm-blooded animal, such as a human being, which comprises administering to said animal an effective amount of a combination of an anti-angiogenic agent and an anti-hypertensive agent.

According to a further aspect of the present invention there is provided the use of a combination of an anti-angiogenic agent and an anti-hypertensive agent for the manufacture of a medicament for producing an anti-angiogenic and/or vascular permeability reducing effect in a warm-blooded mammal, such as a human being.

According to a further aspect of the present invention there is provide a pharmaceutical composition, comprising an anti-angiogenic agent and an anti-hypertensive agent, for producing an anti-angiogenic and/or vascular permeability reducing effect in a warm-blood mammal, such as a human being.

According to a further aspect of the present invention there is provided a pharmaceutical composition, comprising:

a) an anti-angiogenic agent or a pharmaceutically acceptable salt, solvate or pro-drug thereof;

b) an anti-hypertensive agent or a pharmaceutically acceptable salt, solvate or pro-drug thereof; and optionally c) a pharmaceutically acceptable carrier or diluent.

According to a further aspect of the present invention there is provided a method for treating a warm-blooded animal such as a human being, in need of an anti-angiogenic effect comprising administering to said animal:

a) an amount of a first compound, said first compound being an anti-angiogenic agent or a pharmaceutically acceptable salt, solvate or prodrug thereof or a pharmaceutical composition thereof; and b) an amount of a second compound, said second compound being an anti-hypertensive agent or a pharmaceutically acceptable salt, solvate or prodrug thereof or a pharmaceutical composition thereof;

wherein said first compound and said second compound are either administered together or are administered sequentially with either compound administered first.

According to a further aspect of the present invention there is provided a kit, for use in producing an anti-angiogenic effect and/or vascular permeability reducing effect in a warm-blooded animal such as a human being, comprising:

a) an anti-angiogenic agent or a pharmaceutically acceptable salt, solvate or pro-drug thereof or a pharmaceutical composition thereof;

b) an anti-hypertensive or a pharmaceutically acceptable salt, solvate or pro-drug thereof or a pharmaceutical composition thereof; and c) a container means for containing said agents.

As discussed above it is believed that the vasodilation induced by VEGF and FGF is dependent on nitric oxide. Thus, without being bound by theoretical considerations it is believed that the increase in blood pressure induced by a VEGF inhibitor is dependent on modulation of nitric oxide levels.

Thus according to a further aspect of the present invention there is provided a method of treatment of a disease state associated with angiogenesis which comprises the administration of an effective amount of a combination of an anti-angiogenic agent, which affects the level of nitric oxide, and an anti-hypertensive agent to a warm-blooded animal, such as a human being.

According to a further feature of the invention there is provided the use of a combination of an anti-angiogenic agent, which affects the level of nitric oxide, and an anti-hypertensive agent for use in the manufacture of a medicament for the treatment of a disease state associated with angiogenesis in a warm-blooded mammal, such as a human being.

According to a further feature of the invention there is provided a pharmaceutical composition comprising a combination of an anti-angiogenic agent, which affects the level of nitric oxide, and an anti-hypertensive agent for the treatment of a disease state associated with angiogenesis in a warm-blooded mammal, such as a human being.

According to a further aspect of the present invention there is provided a method of treatment of a disease state associated with angiogenesis which comprises the administration of an effective amount of a combination of an anti-angiogenic agent, which blocks the signalling of a tyrosine kinase, and an anti-hypertensive agent to a warm-blooded animal, such as a human being.

According to a further feature of the invention there is provided the use of a combination of an anti-angiogenic agent, which blocks the signalling of a tyrosine kinase, and an anti-hypertensive agent for use in the manufacture of a medicament for the treatment of a disease state associated with angiogenesis in a warm-blooded mammal, such as a human being.

According to a further feature of the invention there is provided a pharmaceutical composition comprising a combination of an anti-angiogenic agent, which blocks the signalling of a tyrosine kinase, and an anti-hypertensive agent for the treatment of a disease state associated with angiogenesis in a warm-blooded mammal, such as a human being.

Tyrosine kinases include both receptor tyrosine kinases and intracellular tyrosine kinases.

Receptor tyrosine kinases include, but are not limited to, receptors for the following growth factors: VEGF, FGF, epidermal growth factor, insulin-like growth factor, insulin, hepatocyte growth factor and platelet-derived growth factor.

Receptor tyrosine kinases include receptors with intrinsic tyrosine kinase activity and receptors which activate associated tyrosine kinases, for example the insulin receptor.

Intracellular tyrosine kinases include, but are not limited to, src and focal adhesion kinase (FAK).

The activity of a tyrosine kinase can be blocked in a number of way including, but not restricted to: inhibiting the tyrosine kinase activity, blocking the binding of a ligand to the receptor for example using an antibody, using a receptor antagonist or altering the conformation of the kinase, for example using a compound which binds to an allosteric site.

The signalling of the tyrosine kinase may be blocked at the level of the tyrosine kinase or may be blocked at a level further down the signalling pathway modulating the activity of a component whose activity is modulated by activation of the tyrosine kinase.

According to a further aspect of the present invention there is provided a method of treatment of a disease state associated with angiogenesis which comprises the administration of an effective amount of a combination of an anti-angiogenic agent, which modulates the activity of a tyrosine kinase having vascular effects, and an anti-hypertensive agent to a warm-blooded animal, such as a human being.

According to a further feature of the invention there is provided the use of a combination of an anti-angiogenic agent, which modulates the activity of a tyrosine kinase having vascular effects, and an anti-hypertensive agent for use in the manufacture of a medicament for the treatment of a disease state associated with angiogenesis in a warm-blooded mammal, such as a human being.

According to a further feature of the invention there is provided a pharmaceutical composition comprising a combination of an anti-angiogenic agent, which modulates the activity of a tyrosine kinase having vascular effects, and an anti-hypertensive agent for the treatment of a disease state associated with angiogenesis in a warm-blooded mammal, such as a human being.

Tyrosine kinases which have vascular effects include, but are not limited to, receptors for the following growth factors: VEGF, FGF, epidermal growth factor, insulin-like growth factor, insulin, hepatocyte growth factor and platelet-derived growth factor.

According to a further aspect of the present invention there is provided a method of treatment of a disease state associated with angiogenesis which comprises the administration of an effective amount of a combination of a tyrosine kinase inhibitor, which modulates the level of nitric oxide, and an anti-hypertensive agent to a warm-blooded animal, such as a human being.

According to a further feature of the invention there is provided the use of a combination of a tyrosine kinase inhibitor, which modulates the level of nitric oxide, and an anti-hypertensive agent for use in the manufacture of a medicament for the treatment of a disease state associated with angiogenesis in a warm-blooded mammal, such as a human being.

According to a further feature of the invention there is provided a pharmaceutical composition comprising a combination of a tyrosine kinase inhibitor, which modulates the level of nitric oxide, and an anti-hypertensive agent for the treatment of a disease state associated with angiogenesis in a warm-blooded mammal, such as a human being.

Tyrosine kinases which modulate the level of nitric oxide include the VEGF receptor and the FGF receptor.

Combinations of the invention may be administered sequentially or may be administered simultaneously. When administered sequentially either the anti-angiogenic agent or the anti-hypertensive agent may be administered first.

An anti-hypertensive is any agent which lowers blood pressure. There are many different categories of anti-hypertensive agents including calcium channel blockers, angiotensin converting enzyme inhibitors (ACE inhibitors), angiotensin II receptor antagonists (A-II antagonists), diuretics, beta-adrenergic receptor blockers (β-blockers), vasodilators and alpha-adrenergic receptor blockers (α-blockers). Any anti-hypertensive agent may be used in accordance with this invention and examples from each class are given hereinafter.

Calcium channel blockers which are within the scope of this invention include, but are not limited to: amlodipine (U.S. Pat. No. 4,572,909); bepridil (U.S. Pat. No. 3,962,238 or U.S. Pat. Reissue No. 30,577); clentiazem (U.S. Pat. No. 4,567,175); diltiazem (U.S. Pat. No. 3,562,257); fendiline (U.S. Pat. No. 3,262,977); gallopamil (U.S. Pat. No. 3,261,859); mibefradil (U.S. Pat. No. 4,808,605); prenylamine (U.S. Pat. No. 3,152,173); semotiadil (U.S. Pat. No. 4,786,635); terodiline (U.S. Pat. No. 3,371,014); verapamil (U.S. Pat. No. 3,261,859); aranidipine (U.S. Pat. No. 4,446,325); barnidipine (U.S. Pat. No. 4,220,649); benidipine (European Patent Application Publication No. 106,275); cilnidipine (U.S. Pat. No. 4,672,068); efonidipine (U.S. Pat. No. 4,885,284); elgodipine (U.S. Pat. No. 4,952,592); felodipine (U.S. Pat. No. 4,264,611); isradipine (U.S. Pat. No. 4,466,972); lacidipine (U.S. Pat. No. 4,801,599); lercanidipine (U.S. Pat. No. 4,705,797); manidipine (U.S. Pat. No. 4,892,875); nicardipine (U.S. Pat. No. 3,985,758); nifedipine (U.S. Pat. No. 3,485,847); nilvadipine (U.S. Pat. No. 4,338,322); nimodipine (U.S. Pat. No. 3,799,934); nisoldipine (U.S. Pat. No. 4,154,839); nitrendipine (U.S. Pat. No. 3,799,934); cinnarizine (U.S. Pat. No. 2,882,271); flunarizine (U.S. Pat. No. 3,773,939); lidoflazine (U.S. Pat. No. 3,267,104); lomerizine (U.S. Pat. No. 4,663,325); bencyclane (Hungarian Patent No. 151,865); etafenone (German Patent No. 1,265,758); and perhexiline (British Patent No. 1,025,578). The disclosures of all such patents and patent applications are incorporated herein by reference.

Angiotensin Converting Enzyme Inhibitors (ACE-Inhibitors) which are within the scope of this invention include, but are not limited to: alacepril (U.S. Pat. No. 4,248,883); benazepril (U.S. Pat. No. 4,410,520); captopril (U.S. Pat. Nos. 4,046,889 and 4,105,776); ceronapril (U.S. Pat. No. 4,452,790); delapril (U.S. Pat. No. 4,385,051); enalapril (U.S. Pat. No. 4,374,829); fosinopril (U.S. Pat. No. 4,337,201); imidapril (U.S. Pat. No. 4,508,727); lisinopril (U.S. Pat. No. 4,555,502); moveltipril (Belgium Patent No. 893,553); perindopril (U.S. Pat. No. 4,508,729); quinapril (U.S. Pat. No. 4,344,949); ramipril (U.S. Pat. No. 4,587,258); spirapril (U.S. Pat. No. 4,470,972); temocapril (U.S. Pat. No. 4,699,905); and trandolapril (U.S. Pat. No. 4,933,361. The disclosures of all such patents are incorporated herein by reference.

Angiotensin-II receptor antagonists (A-II antagonists) which are within the scope of this invention include, but are not limited to: candesartan (U.S. Pat. No. 5,196,444); eprosartan (U.S. Pat. No. 5,185,351); irbesartan (U.S. Pat. No. 5,270,317); losartan (U.S. Pat. No. 5,138,069); and valsartan (U.S. Pat. No. 5,399,578. The disclosures of all such U.S. patents are incorporated herein by reference.

β-Blockers which are within the scope of this invention include, but are not limited to: acebutolol (U.S. Pat. No. 3,857,952); alprenolol (Netherlands Patent Application No. 6,605,692); amosulalol (U.S. Pat. No. 4,217,305); arotinolol (U.S. Pat. No. 3,932,400); atenolol (U.S. Pat. Nos. 3,663,607 and 3,836,671); befunolol (U.S. Pat. No. 3,853,923); betaxolol (U.S. Pat. No. 4,252,984); bevantolot (U.S. Pat. No. 3,857,891); bisoprolol (U.S. Pat. No. 4,258,062); bopindolol (U.S. Pat. No. 4,340,541); bucumolol (U.S. Pat. No. 3,663,570); bufetolol (U.S. Pat. No. 3,723,476); bufuralol (U.S. Pat. No. 3,929,836); bunitrolol (U.S. Pat. No. 3,541,130); bupranolol (U.S. Pat. No. 3,309,406); butidrine hydrochloride (French Patent No. 1,390,056); butofilolol (U.S. Pat. No. 4,302,601); carazolol (German Patent No. 2,240,599); carteolol (U.S. Pat. No. 3,910,924); carvedilol (U.S. Pat. No. 4,503,067); celiprolol (U.S. Pat. No. 4,034,009); cetamolol (U.S. Pat. No. 4,059,622); cloranolol (German Patent No. 2,213,044); dilevalol (Clifton et al., Journal of Medicinal Chemistry, 1982, 25, 670); epanolol (U.S. Pat. No. 4,167,581); indenolol (U.S. Pat. No. 4,045,482); labetalol (U.S. Pat. No. 4,012,444); levobunolol (U.S. Pat. No. 4,463,176); mepindolol (Seeman et al, Helv. Chim. Acta, 1971, 54, 2411); metipranolol (Czechoslovakian Patent Application No. 128,471); metoprolol (U.S. Pat. No. 3,873,600); moprolol (U.S. Pat. No. 3,501,769); nadolol (U.S. Pat. No. 3,935,267); nadoxolol (U.S. Pat. No. 3,819,702); nebivalol (U.S. Pat. No. 4,654,362); nipradilol (U.S. Pat. No. 4,394,382); oxprenolol (British Patent No. 1,077,603); penbutolol (U.S. Pat. No. 3,551,493); pindolol (Swiss Patents Nos. 469,002 and 472,404); practolol (U.S. Pat. No. 3,408,387); pronethalol (British Patent No. 909,357); propranolol (U.S. Pat. Nos. 3,337,628 and 3,520,919); sotalol (Uloth et al., Journal of Medicinal Chemistry, 1966, 9, 88); sulfinalol (German Patent No. 2,728,641); talinolol (U.S. Pat. Nos. 3,935,259 and 4,038,313); tertatolol (U.S. Pat. No. 3,960,891); tilisolol (U.S. Pat. No. 4,129,565); timolol (U.S. Pat. No. 3,655,663); toliprolol (U.S. Pat. No. 3,432,545); and xibenolol (U.S. Pat. No. 4,018,824. The disclosures of all such patents, patent applications and references are incorporated herein by reference.

α-Blockers which are within the scope of this invention include, but are not limited to: amosulalol (U.S. Pat. No. 4,217,305); arotinolol (which may be prepared as described hereinbefore); dapiprazole (U.S. Pat. No. 4,252,721); doxazosin (U.S. Pat. No. 4,188,390); fenspiride (U.S. Pat. No. 3,399,192); indoramin (U.S. Pat. No. 3,527,761); labetolol; naftopidil (U.S. Pat. No. 3,997,666); nicergoline U.S. Pat. No. 3,228,943); prazosin (U.S. Pat. No. 3,511,836); tamsulosin (U.S. Pat. No. 4,703,063); tolazoline (U.S. Pat. No. 2,161,938); trimazosin (U.S. Pat. No. 3,669,968); and yohimbine, which may be isolated from natural sources according to methods well known to those skilled in the art. The disclosures of all such U.S. patents are incorporated herein by reference.

The term "vasodilator", where used herein, is meant to include cerebral vasodilators, coronary vasodilators and peripheral vasodilators. Cerebral vasodilators within the scope of this invention include, but are not limited to: bencyclane (which may be prepared as described hereinbefore); cinnarizine (which may be prepared as described hereinbefore); citicoline, which may be isolated from natural sources as disclosed in Kennedy et al., Journal of the American Chemical Society, 1955, 77, 250 or synthesised as disclosed in Kennedy, Journal of Biological Chemistry, 1956, 222, 185; cyclandelate (U.S. Pat. No. 3,663,597); ciclonicate (German Patent No. 1,910,481); diisopropylamine dichloroacetate (British Patent No. 862,248); eburnamonine (Hermann et al., Journal of the American Chemical Society, 1979, 101, 1540); fasudil (U.S. Pat. No. 4,678,783); fenoxedil (U.S. Pat. No. 3,818,021); flunarizine (U.S. Pat. No. 3,773,939); ibudilast (U.S. Pat. No. 3,850,941); ifenprodil (U.S. Pat. No. 3,509,164); lomerizine (U.S. Pat. No. 4,663,325); nafronyl (U.S. Pat. No. 3,334,096); nicametate (Blicke et al., Journal of the American Chemical Society, 1942, 64, 1722); nicergoline (which may be prepared as described hereinbefore); nimodipine (U.S. Pat. No. 3,799,934); papaverine, which may be prepared as reviewed in Goldberg, Chem. Prod. Chem. News, 1954, 17, 371; pentifylline (German Patent No. 860,217); tinofedrine (U.S. Pat. No. 3,767,675); vincamine (U.S. Pat. No. 3,770,724); vinpocetine (U.S. Pat. No. 4,035,750); and viquidil (U.S. Pat. No. 2,500,444. The disclosures of all such patents and references are incorporated herein by reference.

Coronary vasodilators within the scope of this invention include, but are not limited to: amotriphene (U.S. Pat. No. 3,010,965); bendazol (Feitelson, et al., J. Chem. Soc. 1958, 2426); benfurodil hemisuccinate (U.S. Pat. No. 3,355,463); benziodarone (U.S. Pat. No. 3,012,042); chloracizine (British Patent No. 740,932); chromonar (U.S. Pat. No. 3,282,938); clobenfural (British Patent No. 1,160,925); clonitrate, which may be prepared from propanediol according to methods well known to those skilled in the art, e.g., see Annalen, 1870, 155, 165; cloricromen (U.S. Pat. No. 4,452,811); dilazep (U.S. Pat. No. 3,532,685); dipyridamole (British Patent No. 807,826); droprenilamine (German Patent No. 2,521,113); efloxate (British Patents Nos. 803,372 and 824,547); erythrityl tetranitrate, which may be prepared by nitration of erytliritol according to methods well-known to those skilled in the art; etafenone (German Patent No. 1,265,758); fendiline (U.S. Pat. No. 3,262,977); floredil (German Patent No. 2,020,464); ganglefene (U.S.S.R. Patent No. 115,905); hexestrol bis(β-diethylaminoethyl) ether (Lowe et al., J. Chem. Soc. 1951, 3286); hexobendine (U.S. Pat. No. 3,267,103); itramin tosylate (Swedish Patent No. 168,308); khellin (Baxter et al., Journal of the Chemical Society, 1949, S 30); lidoflazine (U.S. Pat. No. 3,267,104); mannitol hexanitrate, which may be prepared by the nitration of mannitol according to methods well-known to those skilled in the art; medibazine (U.S. Pat. No. 3,119,826); nitroglycerin; pentaerythritol tetranitrate, which may be prepared by the nitration of pentaerythritol according to methods well-known to those skilled in the art; pentrinitrol (German Patent No. 638,422-3); perhexiline (which may be prepared as described hereinbefore); pimefylline (U.S. Pat. No. 3,350,400); prenylamine (U.S. Pat. No. 3,152,173); propatyl nitrate (French Patent No. 1,103,113); trapidil (East German Patent No. 55,956); tricromyl (U.S. Pat. No. 2,769,015); trimetazidine (U.S. Pat. No. 3,262,852); trolnitrate phosphate, which may be prepared by nitration of triethanolamine followed by precipitation with phosphoric acid according to methods well-known to those skilled in the art; visnadine (U.S. Pat. Nos. 2,816,118 and 2,980,699. The disclosures of all such patents and references are incorporated herein by reference.

Peripheral vasodilators within the scope of this invention include, but are not limited to: aluminium nicotinate (U.S. Pat. No. 2,970,082); bamethan (Corrigan et al., Journal of the American Chemical Society, 1945, 67, 1894); bencyclane (which may be prepared as described herein before); betahistine (Walter et al, Journal of the American Chemical Society, 1941, 63, 2771); bradykinin (Hamburg et al., Arch. Biochem. Biophys., 1958, 76 252); brovincamine (U.S. Pat. No. 4,146, 643); bufeniode (U.S. Pat. No. 3,542,870); buflomedil (U.S. Pat. No. 3,895,030); butalamine (U.S. Pat. No. 3,338,899); cetiedil (French Patent No. 1,460,571); ciclonicate (German Patent No. 1,910,481); cinepazide (Belguim Patent No. 730, 345); cinnarizine (which may be prepared as described herein before); cyclandelate (which may be prepared as described hereinbefore); diisopropylamine dichloroacetate (which may be prepared as described hereinbefore); eledoisin (British Patent No. 984,810); fenoxedil (which may be prepared as described hereinbefore); flunarizine (which may be prepared as described hereinbefore); hepronicate (U.S. Pat. No. 3,384, 642); ifenprodil (which may be prepared as described hereinbefore); iloprost (U.S. Pat. No. 4,692,464); inositol niacinate (Badgett et al., Journal of the American Chemical Society, 1947, 69, 2907); isoxsuprine (U.S. Pat. No. 3,056, 836); kallidin (Nicolaides et al., Biochem. Biophys. Res. Commun., 1961, 6, 210); kallikrein (German Patent No. 1,102,973); moxisylyte (German Patent No. 905,738); nafronyl (which may be prepared as described herein before); nicametate (which may be prepared as described herein before); nicergoline (which may be prepared as described hereinbefore); nicofuranose (Swiss Patent No. 366,523); nylidrin (U.S. Pat. Nos. 2,661,372 and 2,661,373); pentifylline (which may be prepared as described hereinbefore); pentoxifylline, which may be prepared as disclosed U.S. Pat. No. 3,422,107); piribedil (U.S. Pat. No. 3,299,067); prostaglandin $E_1$, which may be prepared by any of the methods referenced in the Merck Index, Twelfth Edition, Budaveri, Ed, New Jersey 1996, page 1353); suloctidil (German Patent No. 2,334,404); tolazoline (U.S. Pat. No. 2,161,938); and xanthinol niacinate (German Patent No. 1,102,750 or Korbonits et al, Acta. Pharm. Hung., 1968, 38, 98. The disclosures of all such patents and references are incorporated herein by reference.

The term "diuretic", within the scope of this invention, includes but is not limited to diuretic benzothiadiazine derivatives, diuretic organomercurials, diuretic purines, diuretic steroids, diuretic sulfonamide derivatives, diuretic uracils and other diuretics such as amanozine (Austrian Patent No. 168, 063); amiloride (Belguim Patent No. 639,386); arbutin (Tschitschibabin et al., Annalen, 1930, 479, 303); chlorazanil (Austrian Patent No. 168,063); ethacrynic acid (U.S. Pat. No. 3,255,241); etozolin (U.S. Pat. No. 3,072,653); hydracarbazine (British Patent No. 856,409); isosorbide (U.S. Pat. No. 3,160,641); mannitol; metochalcone (Freudenberg et al., Ber., 1957, 90, 957); muzolimine (U.S. Pat. No. 4,018,890); perhexiline (which may be prepared as described hereinbefore); ticrynafen (U.S. Pat. No. 3,758,506); triamterene (U.S. Pat. No. 3,081,230); and urea. The disclosures of all such patents and references are incorporated herein by reference.

Diuretic benzothiadiazine derivatives within the scope of this invention include, but are not limited to: althiazide (British Patent No. 902,658); bendroflumethiazide (U.S. Pat. No. 3,392,168); benzthiazide (U.S. Pat. No. 3,440,244); benzylhydrochlorothiazide (U.S. Pat. No. 3,108,097); buthiazide (British Patents Nos. 861,367 and 885,078); chlorothiazide (U.S. Pat. Nos. 2,809,194 and 2,937,169); chlorthalidone (U.S. Pat. No. 3,055,904); cyclopenthiazide (Belguim Patent No. 587,225); cyclothiazide (Whitehead et al., Journal of Organic Chemistry, 1961, 26, 2814); epithiazide (U.S. Pat. No. 3,009,911); ethiazide (British Patent No. 861,367); fenquizone (U.S. Pat. No. 3,870,720); indapamide (U.S. Pat. No. 3,565,911); hydrochliorothiazide (U.S. Pat. No. 3,164,588); hydroflumethiazide (U.S. Pat. No. 3,254,076); methyclothiazide (Close et al., Journal of the American Chemical Society, 1960, 82, 1132); meticrane (French Patents Nos. M2790 and 1,365,504); metolazone (U.S. Pat. No. 3,360, 518); paraflutizide (Belguirn Patent No. 620,829); polythiazide (U.S. Pat. No. 3,009,911); quinethazone (U.S. Pat. No. 2,976,289); teclothiazide (Close et al., Journal of the American Chemical Society, 1960, 82, 1132); and trichlormethiazide (deStevens et al., Experientia, 1960, 16, 113). The disclosures of all such patents and references are incorporated herein by reference.

Diuretic sulfonamide derivatives within the scope of this invention include, but are not limited to: acetazolamide (U.S. Pat. No. 2,554,816); ambuside (U.S. Pat. No. 3,188,329); azosemide (U.S. Pat. No. 3,665,002); bumetanide (U.S. Pat. No. 3,806,534); butazolamide (British Patent No. 769,757); chloraminophenamide (U.S. Pat. Nos. 2,809,194, 2,965,655 and 2,965,656); clofenamide (Olivier, Rec. Trav. Chim., 1918, 37, 307); clopamide (U.S. Pat. No. 3,459,756); clorexolone (U.S. Pat. No. 3,183,243); disulfamide (British Patent No. 851,287); ethozolamide (British Patent No. 795,174); furosemide (U.S. Pat. No. 3,058,882); mefruside (U.S. Pat. No. 3,356,692); methazolamide (U.S. Pat. No. 2,783,241); piretanide (U.S. Pat. No. 4,010,273); torsemide (U.S. Pat. No. 4,018,929); tripamide (Japanese Patent No. 73 05,585); and xipamide (U.S. Pat. No. 3,567,777. The disclosures of all such patents and references are incorporated herein by reference.

Further, the anti-hypertensive agents which may be used in accordance with this invention and the pharmaceutically acceptable salts thereof may occur as prodrugs, hydrates or solvates. Said hydrates and solvates are also within the scope of the present invention.

Preferred anti-hypertensive agents of the invention include, calcium channel blockers, A-II antagonists, ACE inhibitors and β-blockers.

More preferred anti-hypertensive agents of the invention include ACE inhibitors, particularly lisinopril and captopril.

The anti-hypertensives described herein are generally commercially available, or they may be made by standard techniques including those described in the references given hereinbefore.

An anti-angiogenic agent is any agent which inhibits the growth and maintenance of new blood vessels. There are many different categories of anti-angiogenic agents which include, but are not limited to: agents which inhibit the action of growth factors; anti-invasive agents; and vascular targeting agents.

Agents which inhibit the action of growth factors include, but not limited to:

(i) receptor antagonists, for example, an anti-VEGF receptor antibody (Genentech, Canadian Patent Application No. 2213833)

(ii) protein kinase C inhibitors;

(iii) tyrosine kinase inhibitors, for example inhibitors of VEGF receptor tyrosine kinase, such as SU 5416, (Sugen, International Patent Application Publication No. WO 96/40116); and (iv) modulators of the signalling of the receptors Tie-1 and/or Tie 2;

(v) inhibitors of protein expression, for example, inhibitors of VEGF expression, such as RPI 4610 (Ribozyme, U.S. Pat. No. 4,987,071).

Anti-invasion agents include matrix metalloproteinase inhibitors and urokinase plasminogen activator receptor antagonist and urokinase plasminogen activator inhibitors. Matrix metalloproteinase inhibitors include: prinomastat (Agouron, U.S. Pat. No. 5,753,653); ilomastat (Glycomed, International Patent Application Publication No. WO 92/9556); marimastat (British Biotechnology, International Patent Application Publication No. WO 94/2447; and batimastat (British Biotechnology, International Patent Application Publication No. WO 90/5719). Urokinase plasminogen activator receptor antagonists include: compounds disclosed in International Patent Application Publication No. WO96/40747 and compounds disclosed in International Patent Application Publication No. WO 2000001802. Urokinase plasminogen activator inhibitors include: compounds disclosed in International Patent Application Publication No. WO 2000005245.

Vascular targeting agents include: Combretastatin A4 (Bristol Myers Squibb, U.S. Pat. No. 4,996,237); and vascular damaging agents described in International Patent Applications Publication Nos. WO 99/02166 (corresponding U.S. Pat. No. 6,423,753) and WO 00/40529 (corresponding U.S. Pat. No. 7,135,502) the entire disclosure of which U.S. patents and applications is incorporated herein by reference. A particularly preferred vascular damaging agent is N-acetyl-colchinol-O-phosphate (Example 1 of WO 99/02166).

Other anti-angiogenic agents include: AE 941 (Neovastat), isolated from shark cartilage (Aeterna, U.S. Pat. Nos. 5,618,925, 5,985,839, and 6,025,334); thalidomide (Celgene, U.S. Pat. No. 5,463,063); and Vitaxin (LM609, an anti-integrin antibody Cell 1994 79 1157-1164).

Preferred anti-angiogenic agents are agents which inhibit the action of growth factors, particularly tyrosine kinase inhibitors. Most preferred are VEGF receptor tyrosine kinase inhibitors.

Preferred VEGF receptor tyrosine kinase inhibitors include those described in International Patent Applications Publication Nos. WO 97/22596 (corresponding U.S. Pat. No. 5,962,458), WO 97/30035 (corresponding U.S. Pat. No. 6,184,225), WO 97/32856 (corresponding U.S. Pat. No. 6,291,455), WO 97/34876 (corresponding U.S. Pat. No. 6,514,971), WO 97/42187 (corresponding U.S. Pat. No. 6,265,411), WO 98/13354 (corresponding U.S. Pat. No. 6,414,148), WO 98/13350 (corresponding U.S. Pat. No. 6,809,097), WO 99/10349 (corresponding U.S. Pat. No. 6,294,532), WO 00/21955 (corresponding U.S. Pat. No. 7,262,201) and WO 00/47212 (corresponding U.S. Pat. No. 7,074,800), the entire disclosure of each of said U.S. patents is incorporated herein by reference.

Preferred VEGF receptor tyrosine kinase inhibitors are described in WO 00/47212 and are of the formula I:

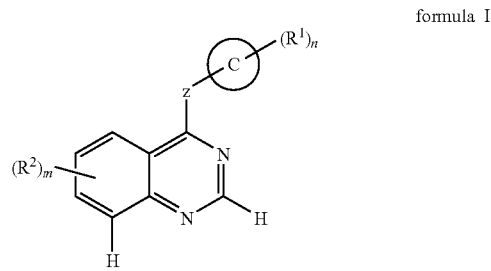

formula I wherein:

ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;

Z is —O—, —NH—, —S—, —CH$_2$— or a direct bond;

n is an integer from 0 to 5;

m is an integer from 0 to 3;

$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or $R^5X^1$— (wherein $X^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, $C_{1-3}$alkyl or $C_{1-3}$alkoxyC$_{2-3}$alkyl), and R$^5$ is selected from one of the following twenty-two groups:

1) hydrogen, oxiranylC$_{1-4}$alkyl or $C_{1-5}$alkyl which may be unsubstituted or which may be substituted with one or more groups selected from hydroxy, fluoro, chloro, bromo and amino;

2) $C_{1-5}$alkylX$^2$C(O)R$^{11}$ (wherein $X^2$ represents —O— or —NR$^{12}$— (in which R$^{12}$ represents hydrogen, $C_{1-3}$alkyl or $C_{1-3}$alkoxyC$_{2-3}$alkyl) and R$^{11}$ represents $C_{1-3}$alkyl, —NR$^{13}$R$^{14}$ or —OR$^{15}$ (wherein R$^{13}$, R$^{14}$ and R$^{15}$ which may be the same or different each represents hydrogen, $C_{1-5}$alkyl or $C_{1-3}$alkoxyC$_{2-3}$alkyl));

3) $C_{1-5}$alkylX$^3$R$^{16}$ (wherein $X^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxyC$_{2-3}$alkyl) and R$^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^4C_{1-5}$alkyl$X^5R^{22}$ (wherein $X^4$ and $X^5$ which may be the same or different are each —O—, —S—, —SO—, —SO$_2$—, —NR$^{23}$C(O)—, —C(O)NR$^{24}$—, —SO$_2$NR$^{25}$—, —NR$^{26}$SO$_2$— or —NR$^{27}$— (wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);

5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkylamino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined herein);
7) $C_{2-5}$alkenyl$R^{28}$ (wherein $R^{28}$ is as defined herein);
8) $C_{2-5}$alkynyl$R^{28}$ (wherein $R^{28}$ is as defined herein);
9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)NR$^{30}$R$^{31}$, —NR$^{32}$C(O)R$^{33}$ (wherein $R^{30}$, $R_{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{29}$ (wherein $R^{29}$ is as defined herein);
11) $C_{2-5}$alkenyl$R^{29}$ (wherein $R^{29}$ is as defined herein);
12) $C_{2-5}$alkynyl$R^{29}$ (wherein $R^{29}$ is as defined herein);
13) $C_{1-5}$alkyl$X^6R^{29}$ (wherein $X^6$ represents —O—, —S—, —SO—, —SO$_2$—, —NR$^{34}$C(O)—, —C(O)NR$^{35}$—, —SO$_2$NR$^{36}$—, —NR$^{37}$SO$_2$— or —NR$^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined herein);
14) $C_{2-5}$alkenyl$X^7R^{29}$ (wherein $X^7$ represents —O—, —S—, —SO—, —SO$_2$—, —NR$^{39}$C(O)—, —C(O)NR$^{40}$—, —SO$_2$NR$^{41}$—, —NR$^{42}$SO$_2$— or —NR$^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined herein);
15) $C_{2-5}$alkynyl$X^8R^{29}$ (wherein $X^8$ represents —O—, —S—, —SO—, —SO$_2$—, —NR$^{44}$C(O)—, —C(O)NR$^{45}$—, —SO$_2$NR$^{46}$—, —NR$^{47}$SO$_2$— or —NR$^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined herein);
16) $C_{1-4}$alkyl$X^9C_{1-4}$alkyl$R^{29}$ (wherein $X^9$ represents —O—, —S—, —SO—, —SO$_2$—, —NR$^{49}$C(O)—, —C(O)NR$^{50}$—, —SO$_2$NR$^{51}$—, —NR$^{52}$SO$_2$— or —NR$^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined herein);

17) $C_{1-4}$alkyl$X^9C_{1-4}$alkyl$R^{28}$ (wherein $X^9$ and $R^{28}$ are as defined herein);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined herein);

21) $C_{2-5}$alkynyl$X^9C_{1-4}$alkyl$R^{28}$ (wherein $X^9$ and $R^{28}$ are as defined herein); and 22) $C_{1-4}$alkyl$R^{54}(C_{1-4}$alkyl)$_q(X^9)_rR^{55}$ (wherein $X^9$ is as defined herein, q is 0 or 1, r is 0 or 1, and $R^{54}$ and $R^{55}$ are each independently selected from hydrogen, $C_{1-3}$allkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino);

$R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosuphony, N-($C_{1-4}$alkylsulphonyl)amino, N-($C_{1-4}$alkylsulphonyl)-N-($C_{1-4}$alkyl)amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ represents a direct bond, —O—, —CH$_2$—, —OC(O)—, —C(O)—, —S—, —SO—, —SO$_2$—, —NR$^{57}$C(O)—, —C(O)NR$^{58}$—, —SO$_2$NR$^{59}$—, —NR$^{60}$SO$_2$— or —NR$^{61}$—, (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl), and $R^{56}$ is selected from one of the following twenty-two groups:

1) hydrogen, oxiranylC$_{1-4}$alkyl or C$_{1-5}$alkyl which may be unsubstituted or which may be substituted with one or more groups selected from hydroxy, fluoro, chloro, bromo and amino;

2) C$_{1-5}$alkyX$^{11}$C(O)R$^{62}$ (wherein X$^{11}$ represents —O— or —NR$^{63}$— (in which R$^{63}$ represents hydrogen, C$_{1-3}$alkyl or C$_{1-3}$alkoxyC$_{2-3}$alkyl) and R$^{62}$ represents C$_{1-3}$alkyl, —NR$^{64}$R$^{65}$ or —OR$^{66}$ (wherein R$^{64}$, R$^{65}$ and R$^{66}$ which may be the same or different each represents hydrogen, C$_{1-5}$alkyl or C$_{1-3}$alkoxyC$_{2-3}$alkyl));

3) C$_{1-5}$alkylX$^{12}$R$^{67}$ (wherein X$^{12}$ represents —O—, —S—, —SO—, —SO$_2$—, —OC(O)—, —NR$^{68}$C(O)—, —C(O)NR$^{69}$—, —SO$_2$NR$^{70}$—, —NR$^{71}$SO$_2$— or —NR$^{72}$— (wherein R$^{68}$, R$^{69}$, R$^{70}$, R$^{71}$ and R$^{72}$ each independently represents hydrogen, C$_{1-3}$alkyl or C$_{1-3}$alkoxyC$_{2-3}$alkyl) and R$^{67}$ represents hydrogen, C$_{1-3}$alkyl, cyclopentyl, cyclohexyl or a 5-6-membered saturated heterocyclic group with 1-2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));

4) C$_{1-5}$alkylX$^{13}$C$_{1-5}$alkylX$^{14}$R$^{73}$ (wherein X$^{13}$ and X$^{14}$ which may be the same or different are each —O—, —S—, —SO—, —SO$_2$—, —NR$^{74}$C(O)—, —C(O)NR$^{75}$—, —SO$_2$NR$^{76}$—, —NR$^{77}$SO$_2$— or NR$^{78}$— (wherein R$^{74}$, R$^{75}$, R$^{76}$, R$^{77}$ and R$^{78}$ each independently represents hydrogen, C$_{1-3}$alkyl or C$_{1-3}$alkoxyC$_{2-3}$alkyl) and R$^{73}$ represents hydrogen, C$_{1-3}$alkyl or C$_{1-3}$alkoxyC$_{2-3}$alkyl);

5) R$^{79}$ (wherein R$^{79}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));

6) C$_{1-5}$alkylR$^{79}$ (wherein R$^{79}$ is as defined herein);

7) C$_{2-5}$alkenylR$^{79}$ (wherein R$^{79}$ is as defined herein);

8) C$_{2-5}$alkynylR$^{79}$ (wherein R$^{79}$ is as defined herein);

9) R$^{80}$ (wherein R$^{80}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —C(O)NR$^{81}$R$^{82}$, —NR$^{83}$C(O)R$^{84}$ (wherein R$^{81}$, R$^{82}$, R$^{83}$ and R$^{84}$, which may be the same or different, each represents hydrogen, C$_{1-4}$alkyl or C$_{1-3}$alkoxyC$_{2-3}$alkyl) and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));

10) C$_{1-5}$alkylR$_{80}$ (wherein R$^{80}$ is as defined herein);

11) C$_{2-5}$alkenylR$^{80}$ (wherein R$^{80}$ is as defined herein);

12) C$_{2-5}$alkynylR$^{80}$ (wherein R$^{80}$ is as defined herein);

13) C$_{1-5}$alkylX$^{15}$R$^{80}$ (wherein X$^{15}$ represents —O—, —S—, —SO—, —SO$_2$—, —NR$^{85}$C(O)—, —C(O)NR$^{86}$—, —SO$_2$NR$^{87}$—, —NR$^{88}$SO$_2$— or —NR$^{89}$— (wherein R$^{85}$, R$^{86}$, R$^{87}$, R$^{88}$ and R$^{89}$ each independently represents hydrogen, C$_{1-3}$alkyl or C$_{1-3}$alkoxyC$_{2-3}$alkyl) and R$^{80}$ is as defined herein);

14) C$_{2-5}$alkenylX$^{16}$R$^{80}$ (wherein X$^{16}$ represents —O—, —S—, —SO—, —SO$_2$—, —NR$^{90}$C(O)—, —C(O)NR$^{91}$—, —SO$_2$NR$^{92}$—, —NR$^{93}$SO$_2$— or —NR$^{94}$— (wherein R$^{90}$, R$^{91}$, R$^{92}$, R$^{93}$ and R$^{94}$ each independently represents hydrogen, C$_{1-3}$alkyl or C$_{1-3}$alkoxy$_{2-3}$alkyl) and R$^{80}$ is as defined herein);

15) C$_{2-5}$alkynylX$^{17}$R$^{80}$ (wherein X$^{17}$ represents —O—, —S—, —SO—, —SO$_2$—, —NR$^{95}$C(O)—, —C(O)NR$^{96}$—, —SO$_2$NR$^{97}$—, —NR$^{98}$SO$_2$— or —NR$^{99}$— (wherein R$^{95}$, R$^{96}$, R$^{97}$, R$^{98}$ and R$^{99}$ each independently represents hydrogen, C$_{1-3}$alkyl or C$_{1-3}$alkoxyC$_{2-3}$alkyl) and R$^{80}$ is as defined herein);

16) C$_{1-4}$alkylX$^{18}$C$_{1-4}$alkylR$^{80}$ (wherein X$^{18}$ represents —O—, —S—, —SO—, —SO$_2$—, —NR$^{100}$C(O)—, —C(O)NR$^{101}$—, —SO$_2$NR$^{102}$—, —NR$^{103}$SO$_2$— or —NR$^{104}$— (wherein R$^{100}$, R$^{101}$, R$^{102}$, R$^{103}$ and R$^{104}$ each independently represents hydrogen, C$_{1-3}$alkyl or C$_{1-3}$alkoxyC$_{2-3}$alkyl) and R$^{80}$ is as defined herein);

17) C$_{1-4}$alkylX$^{18}$C$_{1-4}$alkylR$^{79}$ (wherein X$^{18}$ and R$^{79}$ are as defined herein);

18) C$_{2-5}$alkenyl which may be unsubstituted or which may be substituted with one or more groups selected from hydroxy, fluoro, amino, C$_{1-4}$alkylamino N,N-di(C$_{1-4}$alkyl)amino, aminosulphonyl, N-C$_{1-4}$alkylaminosulphonyl and N,N-di(C$_{1-4}$alkyl)aminosulphonyl;

19) C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N-C$_{1-4}$alkylaminosulphonyl and N,N-di(C$_{1-4}$alkyl)aminosulphonyl;

20) C$_{2-5}$alkenylX$^{18}$C$_{1-4}$alkylR$^{79}$ (wherein X$^{18}$ and R$^{79}$ are as defined herein);

21) C$_{2-5}$alkynylX$^{18}$C$_{1-4}$alkylR$^{79}$ (wherein X$^{18}$ and R$^{79}$ are as defined herein); and 22) C$_{1-4}$alkylR$^{105}$(C$_{1-4}$alkyl)$_x$(X$^{18}$)$_y$R$^{106}$ (wherein X$^{18}$ is as defined herein, x is 0 or 1, y is 0 or 1, and R$^{105}$ and R$^{106}$ are each independently selected from hydrogen, C$_{1-3}$alkyl, cyclopentyl, cyclohexyl and a 5-6-membered saturated heterocyclic group with 1-2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that $R^{105}$ cannot be hydrogen);

and additionally wherein any $C_{1-5}$alkyl, $C_{2-5}$alkenyl or $C_{2-5}$alkynyl group in $R^{56}X^{10}$— may bear one or more substituents selected from hydroxy, halogeno and amino);

or a pharmaceutically acceptable salt, solvate or pro-drug thereof.

Preferred compounds of formula I include:
6-methoxy-4-(2-methylindol-5-yloxy)-7-(3-(pyrrolidin-1-yl)propoxy)quinazoline,
4-(4-fluoroindol-5-yloxy)-6-methoxy-7-(1-methylpiperidin-4-ylmethoxy)quinazoline,
4-(4-fluoroindol-5-yloxy)-6-methoxy-7-(3-(4-methylpiperazin-1-yl)propoxy)quinazoline,
4-(6-fluoroindol-5-yloxy)-6-methoxy-7-(3-(pyrrolidin-1-yl)propoxy)quinazoline,
4-(4-fluoroindol-5-yloxy)-6-methoxy-7-(3-(pyrrolidin-1-yl)propoxy)quinazoline,
4-(4-fluoroindol-5-yloxy)-6-methoxy-7-(3-piperidinopropoxy)quinazoline,
4-(4-fluoro-2-methylindol-5-yloxy)-6-methoxy-7-(3-(pyrrolidin-1-yl)propoxy)quinazoline,
4-(4-fluoro-2-methylindol-5-yloxy)-6-methoxy-7-(3-piperidinopropoxy)quinazoline,
4-(4-fluoro-2-methylindol-5-yloxy)-6-methoxy-7-((1-methylpiperidin-4-yl)methoxy)quinazoline,
4-(4-fluoro-2-methylindol-5-yloxy)-6-methoxy-7-(3-(4-methylpiperazin-1-yl)propoxy)quinazoline,
4-(4-fluoroindol-5-yloxy)-6-methoxy-7-(2-(1-methylpiperidin-4-yl)ethoxy)quinazoline,
(2R)-7-(2-hydroxy-3-(pyrrolidin-1-yl)propoxy)-4-(4-fluoro-2-methylindol-5-yloxy)-6-methoxyquinazoline, and
4-(4-fluoro-2-methylindol-5-yloxy)-6-methoxy-7-(2-(1-methylpiperidin-4-yl)ethoxy)quinazoline, and salts thereof especially hydrochloride salts thereof.

In another aspect of the present invention preferred compounds of formula I include:
4-(4-fluoro-2-methylindol-5-yloxy)-6-methoxy-7-(3-(pyrrolidin-1-yl)propoxy)quinazoline;
4-(4-fluoro-2-methylindol-5-yloxy)-6-methoxy-7-(3-(4-methylpiperazin-1-yl)propoxy)quinazoline;
4-(4-fluoro-2-methylindol-5-yloxy)-6-methoxy-7-(3-piperidinopropoxy)quinazoline;
4-(4-fluoro-2-methylindol-5-yloxy)-6-methoxy-7-((1-methylpiperidin-4-yl)methoxy)quinazoline;
(2R)-7-(2-hydroxy-3-(pyrrolidin-1-yl)propoxy)-4-(4-fluoro-2-methylindol-5-yloxy)-6-methoxyquinazoline; and
4-(4-fluoro-2-methylindol-5-yloxy)-6-methoxy-7-(2-(1-methylpiperidin-4-yl)ethoxy)quinazoline.

A further preferred VEGF receptor tyrosine kinase inhibitor is a compound of the formula II:

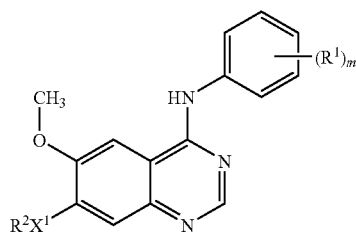

formula (II)

[wherein:
m is an integer from 1 to 3;
$R^1$ represents halogeno or $C_{1-3}$alkyl;
$X^1$ represents —O—;
$R^2$ is selected from one of the following three groups:
1) $C_{1-5}$alkyl$R^{3a}$ (wherein $R^{3a}$ is piperidin-4-yl which may bear one or two substituents selected from hydroxy, halogeno, $C_{1-4}$alkyl, $C_{1-4}$hydroxyalkyl and $C_{1-4}$alkoxy;
2) $C_{2-5}$alkenyl$R^{3a}$ (wherein $R^{3a}$ is as defined hereinbefore);
3) $C_{2-5}$alkynyl$R^{3a}$ (wherein $R^{3a}$ is as defined hereinbefore);
and wherein any alkyl, alkenyl or alkynyl group may bear one or more substituents selected from hydroxy, halogeno and amino;

or a pharmaceutically acceptable salt, solvate or pro-drug thereof.

A more preferred VEGF receptor tyrosine kinase inhibitor is a compound of the formula III:

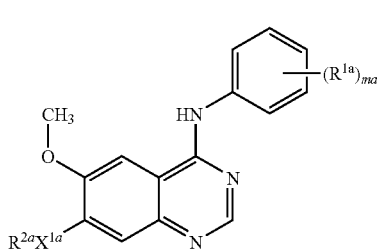

formula (III)

[wherein:
ma is an integer from 1 to 3;
$R^{1a}$ represents halogeno or $C_{1-3}$alkyl;
$X^{1a}$ represents —O—;
$R^{2a}$ is selected from one of the following three groups:
1) $C_{1-5}$alkyl$R^{3a}$ (wherein $R^{3a}$ is as defined herein before in formula II);
2) $C_{2-5}$alkenyl$R^{3a}$ (wherein $R^{3a}$ is as defined herein before in formula II);
3) $C_{2-5}$alkynyl$R^{3a}$ (wherein $R^{3a}$ is as defined herein before in formula II);

or a pharmaceutically acceptable salt, solvate or prodrug thereof.

A particularly preferred VEGF receptor tyrosine kinase inhibitor may be selected from:
4-(4-chloro-2-fluoroanilino)-6-methoxy-7-(1-methylpiperidin-4-ylmethoxy)quinazoline,
4-(2-fluoro-4-methylanilino)-6-methoxy-7-(1-methylpiperidin-4-ylmethoxy)quinazoline,
4-(4-bromo-2-fluoroanilino)-6-methoxy-7-(1-methylpiperidin-4-ylmethoxy)quinazoline, 4-(4-chloro-2,6-difluoroanilino)-6-methoxy-7-(1-methylpiperidin-4-ylmethoxy)quinazoline,
4-(4-bromo-2,6-difluoroanilino)-6-methoxy-7-(1-methylpiperidin-4-ylmethoxy)quinazoline,
4-(4-chloro-2-fluoroanilino)-6-methoxy-7-(piperidin-4-ylmethoxy)quinazoline,
4-(2-fluoro-4-methylanilino)-6-methoxy-7-(piperidin-4-ylmethoxy)quinazoline,
4-(4-bromo-2-fluoroanilino)-6-methoxy-7-(piperidin-4-ylmethoxy)quinazoline,
4-(4-chloro-2,6-difluoroanilino)-6-methoxy-7-(piperidin-4-ylmethoxy)quinazoline,
4-(4-bromo-2,6-difluoroanilino)-6-methoxy-7-(piperidin-4-ylmethoxy)quinazoline, and salts, prodrugs or solvates thereof especially hydrochloride salts thereof.

A further particularly preferred VEGF receptor tyrosine kinase inhibitor is 6-methoxy-4-(2-methylindol-5-yloxy)-7-(3-(pyrrolidin-1-yl)propoxy)quinazoline, and and salts, prodrugs or solvates thereof especially hydrochloride salts thereof.

A further particularly preferred antiangiogenic agent is 4-(4-bromo-2-fluoroanilino)-6-methoxy-7-(2-(1,2,3-triazol-1-yl)ethoxy)quinazoline and salts, prodrugs or solvates thereof especially hydrochloride salts thereof.

An especially preferred antiangiogenic agent is, 4-(4-bromo-2-fluoroanilino)-6-methoxy-7-(1-methylpiperidin-4-ylmethoxy)quinazoline, and salts, prodrugs or solvates thereof especially hydrochloride salts thereof.

It is also to be understood that certain compounds of the formula I, formula II and formula III and salts thereof can exist in solvated as well as unsolvated forms such as, for example, hydrated forms. It is to be understood that the invention encompasses all such solvated forms which inhibit VEGF receptor tyrosine kinase activity.

Various forms of prodrugs are well known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of the formula I, formula II or formula III containing carboxy group is, for example, a pharmaceutically acceptable ester which is hydrolysed in the human or animal body to produce the parent acid, for example, a pharmaceutically acceptable ester formed with a (1-6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), (1-4C)alkyl (such as methyl) or (1-4C)alkoxy (such as ethoxy) group. The term also includes α-acyloxyalkyl esters and related compounds which breakdown to give the parent hydroxy group. Examples of α-acyloxyalkyl esters include acetoxymethoxycarbonyl and 2,2-dimethylpropionyloxymethoxycarbonyl.

An in vivo hydrolysable ester of a compound of the formula I, formula II or formula III containing a hydroxy group is, for example, a pharmaceutically acceptable ester which is hydrolysed in the human or animal body to produce the parent alcohol. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable value for an in vivo hydrolysable amide of a compound of the formula I containing a carboxy group is, for example, a N-(1-6C)alkyl or N,N-di-(1-6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula I, formula II or formula III is, for example, an acid-addition salt of a compound of the formula I, formula II or formula III which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a calcium or magnesium salt, or an ammonium sait, or a salt with an organic base such as methylamine, dimethylamine, trimethylamine, piperidine, morpholine or tris-(2-hydroxyethyl) amine.

The antiangiogenics described herein may be made by standard techniques including those described in the patent applications described hereinbefore which are incorporated herein by reference.

The invention will now be illustrated by the following non-limiting example and with reference to the accompanying FIGURE.

FIG. 1 shows the effect of a VEGF receptor tyrosine kinase inhibitor [4-(4-bromo-2-fluoroanilino)-6-methoxy-7-(1-methylpiperidin-4-ylmethoxy)quinazoline] on the diastolic blood pressure in rats.

EXAMPLE 1

Measurement of Blood Pressure in Conscious Rats by Radio Telemetry

Blood pressure was measured using the Data Sciences radio-telemetry equipment (Data Sciences International, Saint Paul, Minn., USA). This provides a means of measuring the blood pressure (BP), heart rate and activity of a conscious unrestrained rat remotely. The measurements obtained using this system are free from the stresses induced by surgery and restraint. The system comprises a pressure transducer (TA11PA-C40) (the 'implant') implanted in the abdomen of a rat which transmits a radio signal indicating the pressure in the aorta of the animal. The signal is detected by a receiver RA1010 placed under the plastic cage which houses the animal. The signal is evaluated and recorded automatically by pre-written computer software (DataQuest IV installed on an IBM-compatible personal computer, containing an Intel™ 486 processor).

Implantation Methodology

Rats were anaesthetised with "Fluothane™" inhalation anaesthetic. The abdomen of the rat was shaved and the skin coated with a topical disinfectant. An incision was made in the outer skin to expose the abdominal muscle wall which was cut along the mid-line and opened. The viscera of the animal was held back with retractors and the abdominal aorta located. The aorta was cleaned of connective tissue over a 2-3 cm length and carefully separated from the associated vena cava. Care was taken to ensure the area of aorta prepared was below the renal arteries to avoid any potential occlusion of the kidneys following surgery.

A tie was placed loosely under the aorta which was then lifted to occlude the vessel. A puncture was made into the vessel using a 21 gauge needle (Micro Lance, Becton Dickinson) the tip of which had previously been bent to approximately 90 degrees to the needle shaft. Using the bevel of the needle (held in place in the vessel) the tip of the 'implant' catheter was carefully inserted into the vessel. After withdrawal of the needle tip a small drop of surgical glue (Vet Bond 3M) was run down the catheter to form a seal between the catheter and the blood vessel.

The 'implant' was coated with fine mesh which was used to stitch the implant body to the inside of the abdominal wall. The abdominal muscle wall was closed with absorbable stitches. The ends of the stitches were trimmed and the outer skin of the animal was closed using surgical autoclips. These autoclips were removed 7 days after surgery.

General Study Protocol

Male wistar rats were implanted (as described above). Following removal of surgical autoclips all rats were handled daily to acclimatise them to dosing techniques. The animals were then dosed with vehicle (1% polysorbate in water) for a further week.

Blood pressure data was recorded from each animal every 10 minutes throughout the study. The animals were housed in a facility using a 12 hour cycle of light and dark. Normal rat behaviour was seen during the study i.e. the animals rested during the light phase and were active during the dark phase. To obtain more reproducible basal measurements all data reported was obtained during the 12 hour light phase when the test animals were inactive. This average day time blood pressure measurement for each rat was calculated over a 4 day period immediately prior to the commencement of compound dosing.

4-(4-Bromo-2-fluoroanilino)-6-methoxy-7-(1-methylpiperidin-4-ylmethoxy)quinazoline, was dosed p.o. at 12.5 mg/kg once daily for 10 days. For the next 4 days (i.e. days 11 to 14 of compound dosing) the rats were dosed with the ACE inhibitor captopril at 30 mg/kg p.o. once daily in addition to the quinazoline compound. The average blood pressure of each rat was calculated daily and the difference between the daily calculated pressure and the starting pressure was expressed.

FIG. 1 shows the effect of the VEGF receptor tyrosine kinase inhibitor [4-(4-bromo-2-fluoroanilino)-6-methoxy-7-(1-methylpiperidin-4-ylmethoxy)quinazoline] on the diastolic blood pressure in rats. The increase in blood pressure is reversed by the addition of an ACE inhibitor, captopril. Data are presented for a control rat and 3 different rats dosed with the VEGF tyrosine kinase inhibitor.

The invention claimed is:

1. A method for reducing the hypertensive effect of a vascular endothelial growth factor receptor tyrosine kinase inhibitor in a warm-blooded animal to which such inhibitor is being chronically administered as a part of an anti-angiogenic and/or vascular permeability reducing therapy, for the treatment of a disease state selected from cancer, diabetes, psoriasis, rheumatoid arthritis, Kaposi's sarcoma, haemangioma, acute and chronic nephropathies, autoimmune diseases, acute inflammation, excessive scar formation and adhesions, endometriosis, dysfunctional uterine bleeding and ocular diseases with retinal vessel proliferation, said method comprising administering to said animal in combination with said inhibitor an effective amount of an anti-hypertensive agent selected from a calcium channel blocker, an angiotensin II antagonist, an angiotensin converting enzyme inhibitor and a β-blocker, wherein said vascular endothelial growth factor receptor tyrosine kinase inhibitor is selected from:

4-(4-fluoro-2-methylindol-5-yloxy)6-methoxy-7-(3-(pyrrolidin-1-yl)propoxy)quinazoline and 4-(4-bromo-2-fluoroanilino)-6-methoxy-7-(1-methylpiperidin-4-ylmethoxy)quinazoline, and pharmaceutically acceptable salts thereof; and wherein said calcium channel blocker is selected from: amlodipine; bepridil; clentiazem; diltiazem; fendiline; gallopamil; mibefradil; prenylamine; semotiadil; terodiline; verapamil; aranidipine; barnidipine; benidipine; cilnidipine; efonidipine; elgodipine; felodipine; isradipine; lacidipine; lercanidipine; manidipine; nicardipine; nifedipine; nilvadipine; nimodipine; nisoldipine; nitrendipine; cinnarizine; flunarizine; lidoflazine; lomerizine; bencyclane; etafenone; and perhexiline; and wherein said angiotensin II antagonist is selected from candesartan; eprosartan; irbesartan; losartan; and valsartan; and wherein said angiotensin converting enzyme inhibitor is selected from: alacepril; benazepril; captopril; ceronapril; delapril; enalapril; fosinopril; imidapril; lisinopril; moveltipril; perindopril; quinapril; ramipril; spirapril; temocapril; and trandolapril; and wherein said β-blocker is selected from acebutolol; alprenolol; amosulalol; arotinolol; atenolol; befunolol; betaxolol; bevantolol; bisoprolol; bopindolol; bucumolol; bufetolol; bufuralol; bunitrolol; bupranolal; butidrine hydrochloride; butofilolol; carazolol; carteolol; carvedilol; celiprolol; cetamolol; cloranolol; dilevalol; epanolol; indenolol; labetalol; levobunolol; mepindolol; metipranolol; metoprolol; moprolol; nadolol; nadoxolol; nebivalol; nipradilol; oxprenolol; penbutolol; pindolol; practolol; pronethalol; propranolol; sotalol; sulfinalol; talinolol; tertatolol; tilisolol; timolol; toliprolol and xibenolol.

2. The method according to claim 1 wherein the vascular endothelial growth factor receptor tyrosine kinase inhibitor is 4-(4-fluoro-2-methylindol-5-yloxy)-6-methoxy-7- (3-(pyrrolidin-1-yl)propoxy)quinazoline or a pharmaceutically acceptable salt thereof.

3. The method according to claim 1 wherein the vascular endothelial growth factor receptor tyrosine kinase inhibitor is 4-(4-bromo-2-fluoroanilino)-6-methoxy-7-(1-methylpiperidin-4-ylmethoxy)quinazoline or a pharmaceutically acceptable salt thereof.

4. The method according to any one of claims 1, 2 and 3 wherein the anti-hypertensive agent is selected from a calcium channel blocker, an angiotensin converting enzyme inhibitor and a β-blocker.

5. The method according to claim 4 wherein the anti-hypertensive agent is an angiotensin converting enzyme inhibitor.

6. The method according to claim 5 wherein the anti-hypertensive agent is lisinopril or captopril.

* * * * *